United States Patent
Castellanos et al.

(10) Patent No.: US 8,935,097 B2
(45) Date of Patent: Jan. 13, 2015

(54) ARRANGEMENT AND METHOD FOR IDENTIFYING PEOPLE

(75) Inventors: Luis Irais Barzaga Castellanos, Rodgau (DE); Maximilian Fleischer, Höhenkirchen (DE); Elfriede Simon, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 1453 days.

(21) Appl. No.: 12/308,901

(22) PCT Filed: Jun. 6, 2007

(86) PCT No.: PCT/EP2007/055601
§ 371 (c)(1),
(2), (4) Date: Dec. 29, 2008

(87) PCT Pub. No.: WO2008/000606
PCT Pub. Date: Jan. 3, 2008

(65) Prior Publication Data
US 2009/0278659 A1    Nov. 12, 2009

(30) Foreign Application Priority Data

Jun. 29, 2006 (DE) .......................... 10 2006 029 926

(51) Int. Cl.
*G06F 19/22* (2011.01)
*C12Q 1/68* (2006.01)
*A61B 5/117* (2006.01)

(52) U.S. Cl.
CPC ............... *C12Q 1/6813* (2013.01); *A61B 5/117* (2013.01)
USPC ............................................ 702/20; 435/6.1

(58) Field of Classification Search
None
See application file for complete search history.

(56) References Cited

U.S. PATENT DOCUMENTS

2005/0116024 A1 *  6/2005  Beenau et al. ................. 235/380

FOREIGN PATENT DOCUMENTS

| DE | 19717717 A1 | 10/1998 |
| JP | 10151125 A | 6/1998 |
| WO | WO 2004090534 A1 | 10/2004 |

OTHER PUBLICATIONS

Gessner et al. Detection of p53 gene mutations in exhaled breath condensate of non-small cell lung cancer patients. Lung Cancer vol. 43, pp. 215-222 (2004).*
Takahashi et al. Construction of an electrochemical DNA chip for simultaneous genotyping of single nucleotide polymorphisms. Analyst vol. 130, pp. 687-693 (2005).*
Carpagnano et al. 3p Microsatellite Alterations in Exhaled Breath Condensae from Patients with Non-Small Cell Lung Cancer. American Journal of Respiratore and Critical Care Medicine vol. 172, pp. 738-744 (2005).*
Minunni et al. Detection of beta-thalassemia by a DNA piezoelectic biosensor coupled with polymerase chain reaction. Analytica Chimica Acta vol. 481, pp. 55-64 (2003).*
Wooster et al. Instability of short tandem repeats (microsatellites) in human cancers. Nature Genetics vol. 6, pp. 152-156 (1994).*
Hunt et al. Exhaled breath condensate: An evolving tool for noninvasive evaluation of lung disease Journal of Allergy and Clinical Immunology vol. 110, pp. 28-34 (2002).*
Sun et al: "Polymeric microfluidic system for DNA analysis", Analytica Chimica Acta, Elsevier, Amsterdam, NL Bd. 556, Nr.1, 18.01.06, Seiten 80-96.

* cited by examiner

*Primary Examiner* — John S Brusca
(74) *Attorney, Agent, or Firm* — Staas & Halsey LLP

(57) ABSTRACT

A method for identifying people involves breathing respired air into a collector unit, trapping condensate from the respired air in the collector unit, introduction of the condensate by a same introduction to a DNA sensor unit, analysis of the condensate after a cell disruption, comparison of the result the data from a databank and output of the comparison result with analysis of the identity of a person.

18 Claims, 1 Drawing Sheet

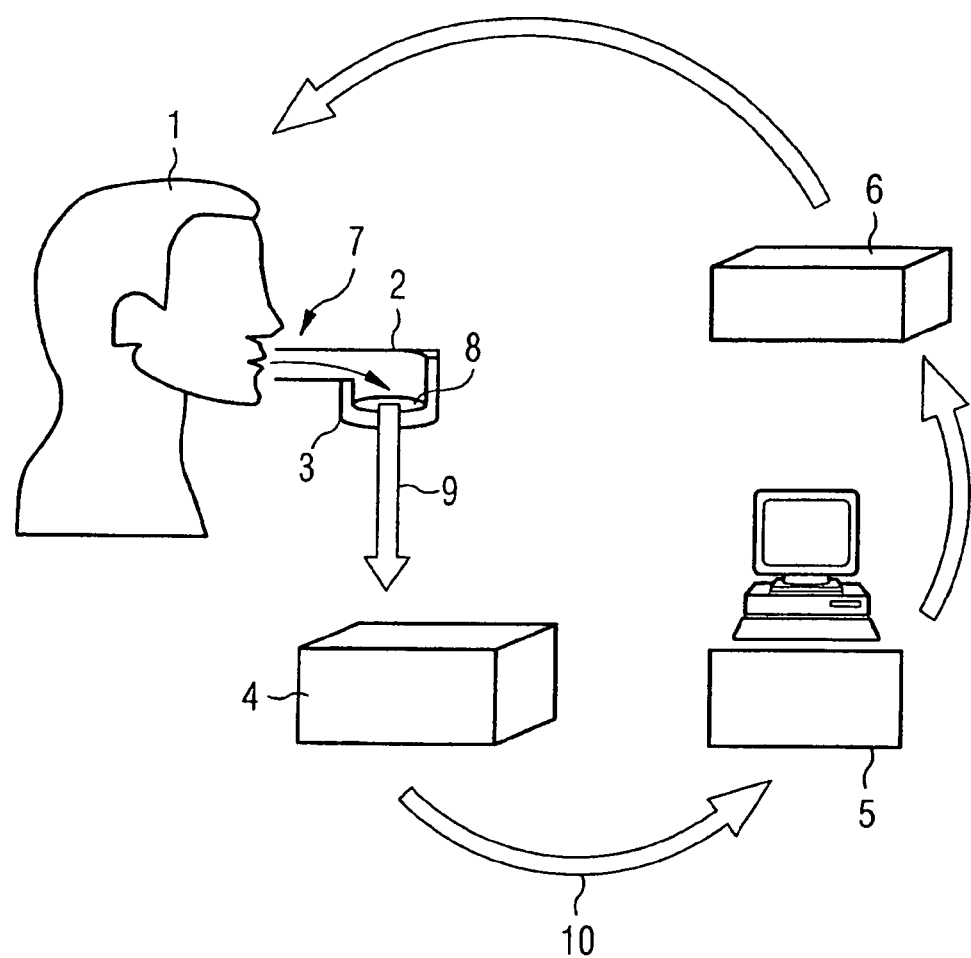

ARRANGEMENT AND METHOD FOR IDENTIFYING PEOPLE

CROSS REFERENCE TO RELATED APPLICATIONS

This application is a national stage application submitted under 35 U.S.C. §371 of International PCT Application No. PCT/EP2007/055601 filed on Jun. 6, 2007, and claims priority to German Application No. 10 2006 029 926.4 filed on Jun. 29, 2006. The contents of International PCT Application No. PCT/EP2007/055601 filed on Jun. 6, 2007 and German Application No. 10 2006 029 926.4 filed on Jun. 29, 2006, are hereby incorporated by reference.

BACKGROUND OF THE INVENTION

The invention relates to an arrangement and a method for identifying persons by recognizing detectable body features. The arrangement is intended to be usable portably.

Determining the identity of a person, or confirming the claimed identity, is one of the most important security tasks in an information technology context. The intention is to be able to distinguish authorized persons from unauthorized persons. The authenticity of persons, and therefore correspondence of a claimed identity with the real identity, must be verifiable. Besides the authentication of persons with the aid of knowledge, for example of a secret number, or possession, for example of a card, i.e. a temporary mechanism, a person is also intended to be assigned so-called attribute features such as physical properties or behavior patterns, which are directly and in general permanently associated with a person. These attribute features may be examined and determined by biometric methods and systems. So-called biometric recognition is carried out with the aid of measurable body features which are assigned to a particular individual. These features are inseparably associated with a person and do not first need to be assigned to them; they cannot be lost and the person does not need to be able to remember them (like a secret number) and they cannot in general be kept secret i.e. these features are apparent, for example face, fingers. Since these features are not transferable, the identity can be assigned uniquely to a person who has been determined correctly by a biometric method.

The demand for reliable person identifications is currently increasing significantly. The problem of person identification is occurring ever more frequently in the field of for example e-commerce, in access control systems, in counter-terrorism etc. Although identification by possession, for example of a pass, still serves its purpose, it is however becoming less important in the modern world with its frequent electronic communication. Biometry has for this reason been gaining importance, particularly in recent times, since it relates the person identification to an individual's features which are unique and to some extent unchangeable, or are stable over a long period of time.

Growing and more complex technologies increasingly require accurate and automated person identification. Access to particular objects can be regulated by particular rights with the aid of person identification. Anyone who has been identified successfully, and therefore accepted, receives the predetermined privileges. When such a method is simpler but also a more reliable, the quality of the person recognition is commensurately better and the acceptance of the biometric method is therefore greater.

A large number of biometric methods are known, the following currently being the methods discussed most fingerprint recognition
face recognition
iris recognition.

Fingerprint Method:

This method has been available for about 100 years for identifying persons. It is used predominantly in the field of criminal prosecution. In the IT-based (information technology) automated form, the digital fingerprint method is a biometric method with high recognition power. For recording the fingerprint in automatic fingerprint recognition, special sensors of optical, capacitive, semiconductor-based, thermal or direct optical technology are used. For example, attempts are being made to measure skin impedances with ultrasound sensors.

Regardless of the nature of the fingerprint recording, the method is always provided with a grayscale image of the finger, i.e. the fingerprint. This image is processed further so that correct matching results (correspondence) can be achieved with the enhanced image. The image processing steps involve for instance reducing the image noise, enhancing the image and detecting the features. The extraction of characteristic traits from the image may be carried out with the aid of various methods. It is possible to record either the entire image, as in global pattern matching, relevant parts thereof or the minutiae of type, position and direction. Comparison of these measured characteristic traits with stored setpoint values shows whether the prints come from the same finger and therefore from one person in particular.

Face Recognition:

In biometric face recognition, a person's face is recorded using a camera and compared with one or more previously stored face images. The image is initially digitized, for example in a PC. The recognition software then locates the face and calculates its characteristic properties. The result of this calculation, the so-called template, is compared with the templates (patterns, models) of the stored face images. The exception to this is when the original image is used as a reference image, which is compared against a current original image for the recognition process.

There are different types of approaches for face recognition, with particular key elements being used. In most face recognition methods, the characteristic features of the facial appearance are determined with the aid of a digitized image. Above all, those features of the face are used which do not change constantly owing to the facial expression, i.e. upper edges of the eye sockets, the regions around the cheekbones and the side parts of the mouth. In principle, comparison of the characteristic facial features with the corresponding reference features is carried out by classical image processing and image analysis methods, for instance, after locating the eyes, calculating the facial features with the aid of a grid network which is placed over the face. One subgroup of biometric face recognition is the so-called eigenface method, which is used above all in the field of person identification. Lastly, there are initial approaches to 3D face recognition.

Iris Recognition:

Between the iris (pigmented tissue) and the cornea of the human eye, there are complex connective tissue structures resembling bands and combs. These structures are different in each individual. They even differ in identical twins. Furthermore, they vary little during a lifetime in a healthy eye. The image of the iris, recorded externally by a conventional camera (for example a CCD camera) allows the structures to be recognized and is therefore suitable as a unique recognition feature.

In individuals with dark eye coloration, however, the structures can be recognized only with difficulty in visible light. Biometric iris recognition systems therefore illuminate the iris from a distance of about one meter with light in the near infrared range, which is virtually invisible to the eye. This penetrates through the "pigment" of the human eye (melanin) better than visible light. A recording of the iris structures can therefore be made for all humans with healthy eyes, without dazzling. From the recorded images, by mathematical methods developed specially for this purpose, a unique data set is formed which serves as a so-called "template" for the biometric recognition.

The other biometric methods include signature recognition, speech or voice recognition, hand geometry or recognition of the typing behavior on a keyboard.

SUMMARY

It is one potential object to provide a biosensor and a corresponding method, so that identification features of persons can be recorded rapidly and reproducibly and a simple check can be carried out which is convenient for the person to be tested. The intention is to provide a simple and mobile design, which is inexpensive.

The inventors realized that person identification can be carried out simply with a sensor which is supplied with exhaled air or with condensate of exhaled air, so-called breath condensate, or with saliva from persons, as a source of identity features or cell material as a measurable sample, and which carries out a DNA analysis, the sensor with its peripherals being mobile. In the sample, there are cells or cell fragments which contain the DNA of the corresponding persons. Analysis of this DNA can be used for identification and recognition of the corresponding person. It is thus possible to ascertain the identity of a person by determination of the DNA from the human cells in the exhaled air condensate of the persons to be verified. This may be subdivided into collection with optional delivery to a biosensor unit, analysis with corresponding comparison with a database and displaying the result. A method for operating the arrangement is likewise provided. The collection of the sample is carried out very simply by blowing into a sample reception system. To this end, a subject is made to blow into a sampler (for example a collection tube with a cold trap) until a sufficient amount of cell material has accumulated.

The DNA analysis system may be an optical, electrical or microgravimetric DNA biosensor. Depending on the way in which the DNA sensor is equipped, the subsequent cell disruption, the PCR (polymerase chain reaction), hybridization and the detection by fragment analysis of the DNA may be carried out directly on a chip or chip card (i.e. on a so-called "lab on a chip"). On the other hand, these various steps may also be performed outside the detection system—in separate steps, so that only the detection step is carried out with the DNA analysis system. Evaluation electronics are provided, for example in the form of a microcontroller or PDA (personal digital assistant), which carries out both the measurement process control and the evaluation of the sensor data, so that the results can then be delivered directly for visualization.

DNA fragment analysis may be carried out by capillary electrophoresis or by Southern blot analysis.

After the DNA fragment analysis, a comparison of the personal data thus obtained is made with an existing database. Person identification can thereby be carried out.

The advantage of such a method is that it can be constructed simply, and can therefore be implemented as an inexpensive and mobile DNA sensor system. This person identification system can thus be set up very simply at various places, operated in situ and made available to a large group of people.

BRIEF DESCRIPTION OF THE DRAWINGS

These and other objects and advantages of the present invention will become more apparent and more readily appreciated from the following description of the preferred embodiments, taken in conjunction with the accompanying drawings of which:

The FIGURE shows a schematic representation of a variant of a person identification system, in which cell material in the exhaled air or in the saliva is analyzed by DNA analytics.

DETAILED DESCRIPTION OF THE PREFERRED EMBODIMENT

Reference will now be made in detail to the preferred embodiments of the present invention, examples of which are illustrated in the accompanying drawing, wherein like reference numerals refer to like elements throughout.

Cell material, which has accumulated on the walls or at the bottom of the sampler by respiratory air and respiratory aerosols condensing out, is removed from the sampler by flushing the system or by suction of the sample and, after cell disruption and the PCR, is delivered directly to the DNA analysis system. Reagents may already be added to the sample. The sample reception system may be used independently of the DNA analysis system, or may be coupled directly to the analysis system.

The person identification system described above has the following advantages:
- very high reliability by DNA analysis,
- non-invasive method, which is straightforward to handle,
- high acceptance when using exhaled air or saliva for the examination, in contrast for example to blood samples and swabs,
- improvement of the person identification in respect of security by DNA analysis,
- simple compact mobile sensor system,
- improvement in the practicability of such an examination since it can be carried out rapidly,
- inexpensive method when using electrical biosensors.

The persons to be identified 1 blow into a flexible sampling system 2 in order to collect the required cell material from the exhaled air 7. By continuously blowing, cells or cell fragments are also exhaled by breath aerosols besides or in biological components of the exhaled air 7. These are deposited on the walls of the sampling system by condensation of the respired air. The blowing into the sampling system must be configured so that the exhalate or saliva contains the required number of cells. This may optionally be done using a controller which determines the collection time or the collection volume. One possible configuration of the sampling system may be a collection tube with a cold trap 3, so that the exhaled air condensate is already pre-collected, or only a simple small tube without a cold trap. Either this sampling system is flexible and independent of the DNA sensor system, and can therefore be used in a mobile fashion and directly in situ, or it is connected directly to the sensor system 4.

After the sampling, the sampling system is coupled to the DNA analysis system and the sample is delivered to the analysis system by flushing or suction. If the sampling system is already coupled to the DNA sensor system 4 in a fixed fashion, the delivery of the sample is carried out by a connected pump or suction device. During the sample transfer 9, the sample may already be supplemented with reagents which are required for the DNA analysis (for example cell lysis medium).

The DNA analysis is then carried out by the DNA sensor system. Optical DNA sensors, for example using fluorescence, chemiluminescence, SPR (surface plasmon resonance) or electrical DNA sensors, for example amperometric, potentiometric, or microgravimetric DNA sensors (piezoelectric, quartz micro-balances) may be used for the DNA analytics. A simple and economical configuration of the sensor system can be achieved by employing electrochemical DNA chips. By integrating the complete system, i.e. cell disruption and sample purification, PCR (polymerase chain reaction), fragment analysis, hybridization and signal readout on a so-called "lab on a chip", a very easily handleable mobile instrument is made available and usable.

The DNA data thus obtained from the DNA fragment analysis are subsequently compared 10 with a DNA database 5 in order to carry out the identification of the person. Depending on the application range, this database may contain only the DNA data of a selected group of people, or it may be linked with a central database when general person identification is required, for example in security checks at airports. The local database is conventionally stored in the instrument, while access to a central database takes place via a radio connection or via a wired network, for example the Internet. Security of the data matching must be ensured by IT security management, likewise the data protection of the persons. In the drawings, reference numeral 6 represents an output or display.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide* v. *DIRECTV*, 69 USPQ2d 1865 (Fed. Cir. 2004).

The invention claimed is:

1. A system to identify persons, comprising:
a collector to receive a condensate from air exhaled by a person to be verified;
a DNA sensor to analyze the person's cell material contained in the condensate and produce measured data; and
a database to compare stored data which includes DNA information corresponding to a plurality of persons, with the measured data to verify an identity of the person,
wherein if the measured data matches the stored data, a predetermined privilege is granted to the person, and
wherein the collector is independent of the DNA sensor, mobile, and directly connectable to the DNA sensor.

2. The system as claimed in claim 1, wherein a display produces a signal output to present results obtained when the stored data is compared with the measured data.

3. The system as claimed in claim 1, wherein the DNA sensor comprises an electrochemical DNA chip to analyze person-specific DNA.

4. The system as claimed in claim 1, wherein the DNA sensor comprises an optical or microgravimetric sensor.

5. The system as claimed in claim 1, wherein DNA fragment analysis is carried out by capillary electrophoresis.

6. The system as claimed in claim 1, wherein DNA fragment analysis is carried out by Southern blot analysis.

7. The system as claimed in claim 1, wherein a cold trap is provided to condense the air exhaled.

8. The system as claimed in claim 1, wherein the collector is replaceable.

9. The system as claimed in claim 2, wherein the DNA sensor comprises an electrochemical DNA chip to analyze person-specific DNA.

10. The system as claimed in claim 2, wherein the DNA sensor comprises an optical or microgravimetric sensor.

11. The system as claimed in claim 10, wherein a cold trap is provided to condense the air exhaled.

12. The system as claimed in claim 11, wherein the collector is replaceable.

13. A method for identifying persons, comprising:
receiving exhaled air into a collector;
trapping condensate from the exhaled air in the collector;
delivering the condensate via a sample delivery to a DNA sensor;
purifying the condensate after cell disruption;
enriching DNA from the condensate using polymerase chain reaction (PCR) primers;
hybridizing the DNA with matching gene probes in the DNA sensor or fragment analysis by capillary electrophoresis or fragment analysis by Southern blot analysis;
analyzing the DNA to produce measured data;
comparing the measured data with DNA information stored in a database which includes DNA information corresponding to a plurality of persons, to verify an identity of the person; and
outputting or displaying an evaluation of a person's identity based on the comparison,
wherein if the measured data matches the stored data, a predetermined privilege is granted to the person, and
wherein the collector is independent of the DNA sensor, mobile, and directly connectable to the DNA sensor.

14. The method as claimed in claim 13, wherein the condensate is delivered to the DNA sensor unit by flushing the condensate from the collector.

15. The method as claimed in claim 14, wherein the condensate is flushed with a Tris buffer or with a phosphate buffer.

16. The method as claimed in claim 15, wherein short tandem repeats (STR) primers are used as PCR primers.

17. The system as claimed in claim 1, wherein the condensate is delivered to the DNA sensor by flushing or suction using a pump or suction device, when the collector is directly connected to the DNA sensor.

18. The method as claimed in claim 13, further comprising:
delivering the condensate to the DNA sensor by flushing or suction using a pump or suction device, when the collector is directly connected to the DNA sensor.

* * * * *

UNITED STATES PATENT AND TRADEMARK OFFICE
CERTIFICATE OF CORRECTION

PATENT NO. : 8,935,097 B2  
APPLICATION NO. : 12/308901  
DATED : January 13, 2015  
INVENTOR(S) : Luis Irais Barzaga Castellanos et al.

Page 1 of 1

It is certified that error appears in the above-identified patent and that said Letters Patent is hereby corrected as shown below:

On the Title Page, References Cited

Column 2, Item [56] (Other Publications), Line 8, Delete "Condensae" and insert -- Condensate --, therefor.

Column 2, Item [56] (Other Publications), Line 11, Delete "piezoelectic" and insert -- piezoelectric --, therefor.

In the Claims

Column 6, line 43, In Claim 14, delete "sensor unit" and insert -- sensor --, therefor.

Signed and Sealed this  
Fifth Day of May, 2015

Michelle K. Lee  
*Director of the United States Patent and Trademark Office*